United States Patent [19]

Poncy et al.

[11] 3,999,549

[45] Dec. 28, 1976

[54] CATAMENIAL TAMPON HAVING FLUID TRANSMISSIVE AND RESILIENT OUTER SHEATH

[76] Inventors: Richard P. Poncy; Mark P. Poncy; George W. Poncy, Sr.; George W. Poncy, Jr.; Robert C. Brandriff, all of 3670 E. Indus. Way, Riviera Beach, Fla. 33404

[22] Filed: June 17, 1975

[21] Appl. No.: 587,677

[52] U.S. Cl. .............................................. 128/285
[51] Int. Cl.² ........................................ A61F 13/20
[58] Field of Search ................... 128/285, 263, 270

[56] References Cited
UNITED STATES PATENTS

| | | | |
|---|---|---|---|
| 1,555,708 | 9/1925 | Gale | 128/285 |
| 1,575,123 | 3/1926 | Martocci-Pisculli | 128/270 |
| 2,676,594 | 4/1954 | Milcent | 128/285 |

*Primary Examiner*—Lawrence W. Trapp
*Attorney, Agent, or Firm*—Lane, Aitken, Dunner & Ziems

[57] ABSTRACT

A catamenial tampon comprising an elongated core of conventional highly absorbent fibrous material which is relatively incompressible and enclosed by a sheath of open-celled resilient foam. The foam transmits by capillary action, fluids from the exterior of the tampon inwardly to the fibrous core. The reticulated foam sheath also isolates the core from the effects of compression which may be caused by muscular activity or by withdrawal.

8 Claims, 4 Drawing Figures

CATAMENIAL TAMPON HAVING FLUID TRANSMISSIVE AND RESILIENT OUTER SHEATH

BACKGROUND OF THE INVENTION

This invention relates to fluid receptors for use within cavities of the human body and more particularly, it concerns improvements in intravaginal catamenial tampons.

Intravaginal tampons are in common use by women for the retention of fluids or menses discharged along the walls of the vagina during the menstrual cycle. Such tampons are usually formed of absorbent materials such as cotton, rayon cellulose wading, synthetic sponge, cellulose fluff, synthetic fibers or combinations of these materials and compressed or molded usually to a generally cylindrical configuration of a size to fit within the vaginal tract.

Several problems are associated with the use of intravaginal tampons for the collection and retention of menstrual fluids. For example, the peripheral interior contour of the vaginal wall, being unpredictably irregular as compared with the preformed tampon often leads to the by-pass of fluid menses through the occasional spaces encountered between the outer surface of the tampon and the inner vaginal wall. If the tampon itself is sufficiently flexible or compressible to conform with the peripheral configuration of the vaginal tract, the compressibility of the tampon itself reduces the effectiveness of the tampon to retain or store the menstrual fluids. In particular, compression of the tampon will result in the discharge of accumulated fluids both when the tampon is compressed directly such as during withdrawal or indirectly due to the increase in intravaginal pressure caused by the most common of body movements.

Because of the configuration of the vaginal tract and nature of menstrual fluid flow, conventional fibrous tampons fall short of full utilization of saturation capacity. Specifically, the menstrual fluids flow down along the walls of the vagina and tend to be collected at the frontal end of the tampon whereas the major absorptive surface exposure is along the sides of the tampon adjacent the vaginal walls. At this area however, the direction of fluid flow is perpendicular to the tampon surface and thus less than ideal for full absorption into the tampon. Finally, and perhaps because of the aforementioned difficulties, the use of tampons is commonly accompanied with undesirable irritation as a result of frequent insertion and withdrawal during periods of heavy menses flow. Also chafing may occur during periods of light menses flow because of the tendency of the tampon to absorb whatever small amount of liquids are present on the vaginal walls thereby to generate excess friction between the tampon and the vaginal walls.

SUMMARY OF THE PRESENT INVENTION

In accordance with the present invention, the difficulties heretofore experienced with intravaginal catamenial tampons are substantially alleviated by enveloping a conventional non-compressible fibrous tampon in a compressible, open-celled or reticulated hydrophilic foam which transfers by capillary action menstrual fluids from the vaginal wall to the fibrous material which in the overall tampon of the invention is in the nature of a non-compressible core. The compressibility of the exterior foam layer allows the tampon to be easily inserted and also to maintain a constant yet gentle pressure about the interior of the vaginal walls. Moreover, because the foam is pocketed with enumerable openings or pores on the surface thereof in contact with the vaginal wall, a full transfer of fluid from the vaginal wall to the formed surface is assured. Because the inner absorbent core maintains a greater affinity for fluid than the non-absorbent vaginal walls surrounding the entire tampon, the direction of capillary action through the open-celled hydrophilic foam is toward the core. This factor is particularly significant during periods of strenuous muscular activity which would lead to the compression of the foam envelope or outer layer. In other words, the direction of capillary action is such that upon compression of the foam, the fluid is discharged to the core as distinguished from outwardly of the foam. The removal of the tampon of the invention is effected conventionally by a drawstring appropriately anchored in the fibrous core. To prevent wicking of fluids along the string, the lower or posterior end portion of the foam envelope is fused such as by heat or ultrasonic fusion thereby to provide an impervious outer skin on the foam envelope over the end portion facing in the direction of the vaginal opening.

Accordingly, among the objects of the present invention are: the provision of an improved tampon particularly suited for intravaginal use; the provision of such a tampon by which the storage capacity for menstrual fluids is significantly increased over tampons of the prior art; the provision of such an improved intravaginal tampon in which the capacity for retention of menstrual fluids is unaffected by compression whether such compression is as a result of removal of the tampon or as a result of muscular activity causing a contraction of the vaginal cavity; and the provision of such an intravaginal tampon which is easily inserted and withdrawn, non-irritating in use and highly effective in its capacity for retention of menstrual fluids.

Other objects and further scope of applicability of the present invention will become apparent from the detailed description to follow taken in conjunction with the accompanying drawings in which like parts are designated by like reference numerals.

DETAILED DESCRIPTION OF THE PREFERRED EMBODIMENT

Figure 1:
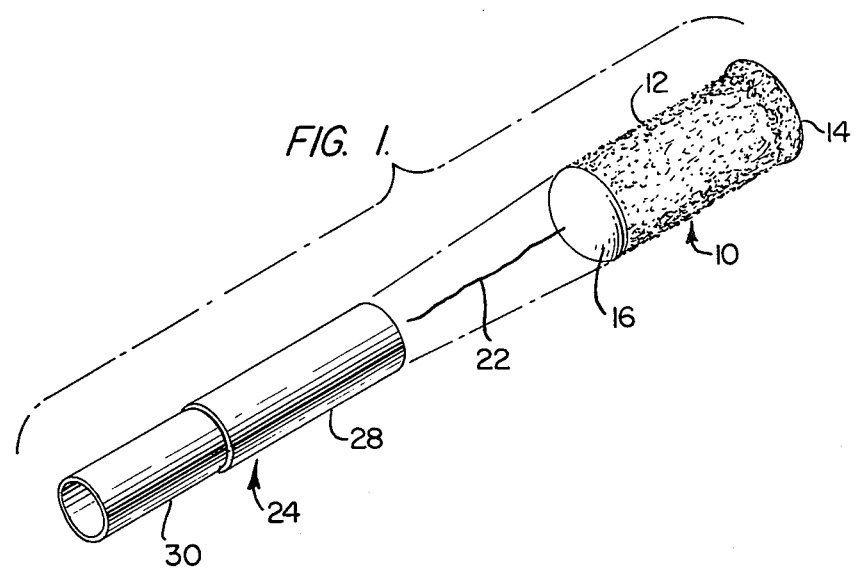
FIG. 1 is an exploded perspective view illustrating the relation of the improved tampon of this invention with respect to a telescopic applicator.
Figure 2:
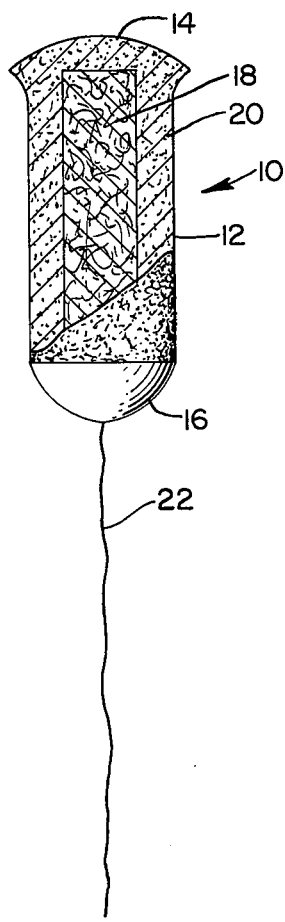
FIG. 2 is an elevation of the tampon in partial cross-section.

In FIGS. 1 and 2 of the drawing, the improved tampon of the present invention is generally designated by the reference numeral 10 and shown in its relaxed or initial condition to establish an essentially cylindrical body 12 having an outwardly flared and dome-like frontal or upper end 14 and a lower or posterior end 16 of essentially hemispherical configuration. The interior construction of the tampon is shown in FIG. 2 to include a central core 18 of relatively non-compressible absorbent fibrous material completely encased, in the disclosed embodiment, by an envelope or sheath of resilient, open-celled or reticulated foam 20. Although the dimensions and in some instances the illustrated exterior shape of the tampon 10 may vary, a conventionally elongated cylindrical shape of approximately ⅞ inch in diameter with the foam sheath in a relaxed condition is preferred for tampons to be used by normal adult women. Of this diameter the foam sheath would account for ½ inch (¼ inch X 2) and the core for the remaining ⅜ inch.

A removal cord 22 is anchored in the core 18 and extends through the lower end 16 of the sheath 20 to be accessible for removal of the tampon 10 after use. As will be more apparent from the description of the composition of the sheath 20 to follow below, the open cells of the reticulated foam structure extend through the exterior surfaces of the foam sheath 20 as minute pores throughout the periphery of the body 12 and the frontal end 14. It is preferred, however, that the posterior end 16 be provided with an impervious skin sealed about the draw cord 22 to prevent any possibility of fluids passing through the posterior end 16 directly from the core 18 or as a result of wicking along the draw cord 22. Such a skin is readily formed by heat or ultrasonic fusion of the exterior foam surface extending about the posterior end 16 to effect a fused layer or impermeable skin about the end 16.

Figure 3:
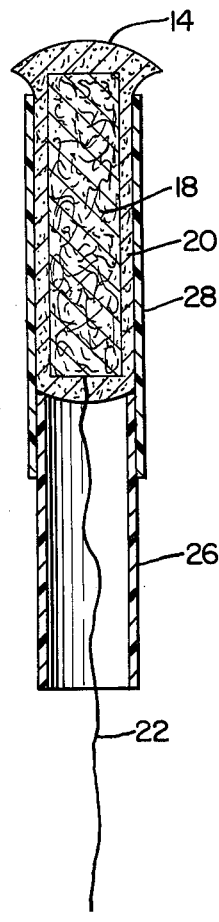
FIG. 3 is a vertical section of the tampon disposed in the telescopic applicator shown in FIG. 1 prior to its insertion.

The tampon 10 is adapted to be inserted using a conventional applicator 24 as shown in FIGS. 1 and 3, which includes inner and outer telescopic tubes 26 and 28, respectively of cardboard or other suitable material conventionally employed for the insertion of catamenial tampons. As can be seen from FIG. 3 of the drawings, the outwardly flared configuration of the frontal end 14 of the sheath 18 provides a protective cushion partially about the insertion end of the tube 28.

As above indicated, the core 18 is highly absorbent and relatively non-compressible particularly in relation to the compressibility of the resilient sheath 20. Although the specific structure of the core, in itself, or the material from which it is formed may vary, a preferred core for tampons of the invention intended for use by normal adult women is provided by a conventional tampon available commercially under the trademark "Junior Tampax" and manufactured by Tampax, Incorporated. The construction of such absorbent devices is fully disclosed in U.S. Pat. No. 3,371,666 issued Mar. 5, 1968 to Albert W. Lewing and accordingly the disclosure of that patent is incorporated by reference herein.

Figure 4:
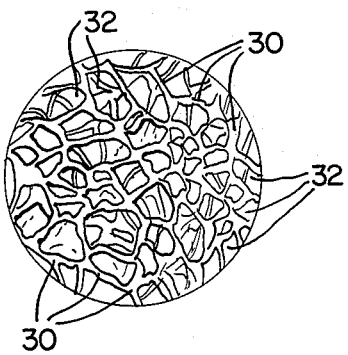
FIG. 4 is a greatly enlarged view depicting the cell construction of the resilient foam employed in the tampon of the invention.

The sheath 20 is preferably formed from reticulated polyurethane foam having in excess of 60 pores per linear inch and preferably about 80 pores per linear inch. A complete disclosure of such foams and their method of manufacture is found in U.S. Pat. No. 3,171,820 issued Mar. 2, 1965 to R. Robert A. Volz and U.S. Pat. No. 3,175,025 issued Mar. 23, 1965. It will suffice for purposes of the present invention to note that the physical structure of such foams, as shown in FIG. 4 of the appended drawings, is in the nature of an open skeletal network 30 about open cells 32 which are interconnected to form minute passages through the skeletal network. The material of the reticulated foam may be made hydrophilic during manufacture or treated subsequently by appropriate wetting agents to achieve an appropriate affinity of the skeletal network 30 to liquid and particularly menstrual fluids. The disclosures of the aforementioned U.S. patents are incorporated herein by reference to provide a full appreciation of the chemical composition of the foam and as well as their methods for the manufacture of such foam.

The selection of a reticulated polyurethane foam having at least 60 and preferably 80 pores per linear inch is predicated principally on the measure of transmissibility of menstrual fluids exhibited by such foams with relatively small pore sizes. For example, reticulated polyurethane having less than 60 pores per linear inch will have incomplete transmission of the menstrual fluids to the fibrous core 18 and a corresponding leakage of the fluids from the sheath on compression thereof. With reticulated polyurethane foams having eighty pores per linear inch, the transfer of fluids to the fibrous core, believed to be the result of a substantially uni-directional capillary gradient, has been found not only completely devoid of discomfort in use but also to effectively isolate the storage of fluids in the fibrous core 18. Also, reticulated polyurethane foams of larger individual pore size or which may be characterized as having a smaller number of pores per linear inch tend to exhibit an uncomfortable or irritating coarseness to the walls of the vagina.

In light of the capacity for the reticulated polyurethane foam sheath to transmit the fluids to the absorbent core 18 in an apparent, exclusively inward direction, compression of the sheath which may occur during use as a result of muscular activity augments the transmission of fluids inwardly as distinguished from expelling the fluids outwardly from the tampon 10. Moreover, compression of the sheath during withdrawal of the tampon after use is without discharge of stored fluids which might otherwise occur by compression of the core 18 itself.

Thus it will be appreciated that by this invention there is provided a highly improved tampon by which the aforementioned objectives are completely fulfilled. It is contemplated that variations may be made in the physical configuration and compositions described without departure from the invention. It is expressly intended, therefore, that the foregoing description is illustrative of a preferred embodiment, not limiting, and that the true spirit and scope of the present invention be determined by reference to the appended claims.

We claim:

1. A catamenial tampon comprising:
    a core of highly absorbent, relatively non-compressible material; and
    a sheath of resilient, open-celled, hydrophilic and fluid transmissive foam about said core;
    the fluid transmissive characteristics of said foam and the fluid absorptive characteristics of said fibrous material being such that after use resulting in substantial storage of menstrual fluid in the tampon, the storage is sufficiently isolated in said core that compression of said sheath upon withdrawal will not cause discharge of fluid from said sheath.

2. The tampon recited in claim 1 wherein said foam is further characterized as having at least 60 open cells per linear inch.

3. The tampon recited in claim 1 wherein said sheath completely encloses said core to provide an exterior configuration established by a generally cylindrical body portion having frontal and posterior ends, said posterior end having an impervious skin covering the surface thereof.

4. The tampon recited in claim 3 including a removal cord extending from said core through said posterior end, said impervious skin being sealed with said cord to prevent wicking of fluids from said core through said posterior end.

5. The tampon recited in claim 1 wherein the diameter of said cylindrical body portion is on the order of ⅞ inch and wherein the radial thickness of said sheath is approximately ¼ inch.

6. The tampon recited in claim 1 wherein said sheath is formed of hydrophilic, reticulated, polyurethane foam.

7. The tampon recited in claim 1 wherein said foam is further characterized as having about 80 open cells per linear inch.

8. A catamenial tampon comprising:
- a core of highly absorbent, relatively non-compressible, fibrous material;
- a sheath of resilient open-celled fluid transmissive foam about said core;
- an applicator tube surrounding said sheath, the insertion end of said sheath extending axially beyond the insertion end of said applicator tube and being enlarged to extend radially from the outer dimension of said tube to provide a protective cushion about the insertion end of said tube.

* * * * *

UNITED STATES PATENT OFFICE
CERTIFICATE OF CORRECTION

Patent No. 3,999,549      Dated December 28, 1976

Inventor(s) Richard P. Poncy et al

It is certified that error appears in the above-identified patent and that said Letters Patent are hereby corrected as shown below:

Column 1, line 23, "performed" should be --preformed--.

Column 4, claim 1, line 7, delete "fibrous".

Signed and Sealed this

Nineteenth Day of April 1977

[SEAL]

Attest:

RUTH C. MASON
*Attesting Officer*

C. MARSHALL DANN
*Commissioner of Patents and Trademarks*